United States Patent
Lagodzki et al.

(10) Patent No.: US 9,427,219 B2
(45) Date of Patent: Aug. 30, 2016

(54) DELIVERY DEVICE FOR VASCULAR OCCLUDING DEVICE

(71) Applicant: Cook Medical Technologies LLC, Bloomington, IN (US)

(72) Inventors: Karol Lagodzki, Bloomington, IN (US); Vanessa Weisman, Bloomington, IN (US); Trevor Plassman, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 715 days.

(21) Appl. No.: 13/680,219

(22) Filed: Nov. 19, 2012

(65) Prior Publication Data

US 2014/0142589 A1    May 22, 2014

(51) Int. Cl.
*A61M 29/00* (2006.01)
*A61B 17/00* (2006.01)
*A61B 17/12* (2006.01)
*A61M 25/09* (2006.01)

(52) U.S. Cl.
CPC ..... *A61B 17/0057* (2013.01); *A61B 17/12022* (2013.01); *A61B 2017/1205* (2013.01); *A61M 25/09041* (2013.01)

(58) Field of Classification Search
CPC .............. A61M 5/344–5/345; A61B 17/0057; A61B 2017/1205; A61F 6/20–6/24
USPC ........ 606/200, 108, 191, 113, 114; 623/1.11; 128/831, 843; 604/533, 539, 103, 264
See application file for complete search history.

(56) References Cited

U.S. PATENT DOCUMENTS

| | | | |
|---|---|---|---|
| 5,746,734 A | 5/1998 | Dormandy, Jr. et al. | |
| 5,895,410 A | 4/1999 | Forber et al. | |
| 5,984,944 A | 11/1999 | Forber | |
| 6,458,137 B1 | 10/2002 | Klint | |
| 6,540,725 B1 * | 4/2003 | Ponzi | 604/272 |
| 7,367,980 B2 | 5/2008 | Kida et al. | |
| 8,043,325 B2 | 10/2011 | Schrodt | |
| 8,123,759 B2 | 2/2012 | Kida et al. | |
| 2004/0098024 A1 * | 5/2004 | Dieck et al. | 606/200 |
| 2005/0090764 A1 * | 4/2005 | Wang | 600/564 |
| 2007/0106324 A1 * | 5/2007 | Garner et al. | 606/200 |
| 2010/0004672 A1 | 1/2010 | Shirley et al. | |
| 2010/0022951 A1 | 1/2010 | Ferrera et al. | |

\* cited by examiner

*Primary Examiner* — Todd E Manahan
*Assistant Examiner* — Majid Jamialahmadi
(74) *Attorney, Agent, or Firm* — Brinks Gilson & Lione

(57) ABSTRACT

A delivery device for delivering material into a catheter through a catheter port includes a cannula having a generally tubular shape and a distal end and a stability collet having a distal attachment portion configured to attach the stability collet to a catheter port. The stability collet has a longitudinal channel through which the cannula extends. The longitudinal channel is dimensioned to allow a longitudinal movement of the cannula in the longitudinal channel. The delivery device further includes an elastic member acting between the cannula and the stability collet. The elastic member biases the cannula distally relative to the stability collet. Thus, when the stability collet is attached to the catheter port, the cannula is urged toward the catheter port, thus reducing a risk of improper alignment between the cannula and the catheter port.

9 Claims, 5 Drawing Sheets

DELIVERY DEVICE FOR VASCULAR OCCLUDING DEVICE

TECHNICAL FIELD

The present invention relates to a delivery device for the delivery of a vascular occluding device. Specifically, the present invention relates to a delivery device for feeding an elongated occluding device, such as an embolization coil, into a catheter port.

BACKGROUND OF THE INVENTION

Elongated occluding devices, such as embolization coils, are typically prepackaged in a loading cannula. Most also incorporate a stability collet designed to provide radial stability to the cannula for proper alignment inside a catheter port.

For delivering the occluding device into the catheter port, the distal end of the cannula must be aligned with a longitudinal bore distally adjacent a catheter well. If the occluding device exits the distal cannula end while a gap exists between the distal cannula end and the longitudinal bore, the coil may not enter the longitudinal bore and may instead curl up in the catheter well. As a result of such a premature delivery of the coil in the catheter port, the coil, the loading cannula, and possibly also the catheter, are discarded.

It is an object of the present invention to reduce such waste.

SUMMARY OF THE INVENTION

According to a first aspect of the present invention, a delivery device is provided for delivering material into a catheter through a catheter port. The delivery device comprises a cannula having a generally tubular shape and a distal end; a stability collet having a distal attachment portion configured to attach the stability collet to a catheter port and a longitudinal channel through which the cannula extends. The longitudinal channel is dimensioned to allow a longitudinal movement of the cannula in the longitudinal channel. The delivery device further comprises an elastic member acting between the cannula and the stability collet. The elastic member biases the cannula distally relative to the stability collet. Thus, when the stability collet is attached to the catheter port, the cannula is urged toward the catheter port, thus reducing a risk of improper alignment between the cannula and the catheter port.

According to another aspect of the invention, the elastic member may be a resilient spring. For example, the resilient spring may be a helical spring.

According to a further aspect of the invention, the resilient spring may be a compression spring with a proximal spring end restricted by the longitudinal channel of the stability collet and with a distal spring end restricted by a stop on the cannula.

According to yet another aspect of the invention, the resilient spring may alternatively be an extension spring arranged with a distal spring end retained by the stability collet and a proximal spring end retained on the cannula. The distal spring end of the extension spring may, for example, be retained by a retainer formed on a proximal portion of the stability collet.

According to one aspect of the invention, the elastic member may be an elastomeric expansion element having a distal element end engaging the stability collet and a proximal element end engaging the cannula.

According to another aspect of the invention, the elastomeric expansion element may have a plurality of stretchable bands extending from the proximal element end to the distal element end.

According to a further aspect of the invention, the elastomeric expansion element may further have a unitary annular sealing portion adjacent the attachment portion of the stability collet, the sealing portion configured to seal the attachment portion against a catheter port to prevent leakage. The elastomeric expansion element may thus perform a dual function of biasing the cannula and of sealing a transition between the stability collet and the catheter port.

According to yet another aspect of the invention, the proximal element end is located outside the stability collet so that the proximal element end is located proximally from the stability collet.

Alternatively, the proximal element end may be located in a cavity of the stability collet. Accordingly, the entire elastic member may be accommodated inside the stability collet.

According to one aspect of the invention, the elastic member has a relaxed state and a tensioned state. The elastic member is in the tensioned state when the distal end of the cannula is in a position relative to the stability collet that corresponds to a position that the distal end of the cannula occupies when a catheter port is attached to the stability collet. In the relaxed state, the elastic member positions the distal end of the cannula distally from the tensioned state. Thus, during attachment of the stability collet to the catheter port, the cannula is urged distally relative to the stability collet as soon as the catheter port displaces the cannula proximally from the relaxed state.

According to another aspect of the invention, the elastic member acts on the cannula via a stop fixedly connected to the cannula. The stop restricts a longitudinal movement of one end of the elastic member relative to the cannula in a least one direction. Depending on the type of elastic element, compression or expansion, the stop is placed to resist a force exerted by the elastic element. Alternatively, the stop may restrict all longitudinal movements of the respective end of the elastic member, i.e. in both longitudinal directions.

According to a further aspect of the invention, the elastic member may fixedly attached to at least one of the cannula and the stability collet.

According to yet another aspect of the invention, the delivery device also includes an elongated occluding device stored in the cannula for delivery to the catheter port.

Further details and advantages will become apparent from the following description of the included drawings depicting various embodiments.

BRIEF DESCRIPTION OF THE DRAWINGS

The attached drawings are included for illustrative purposes only and are not intended to limit the scope of the present invention.

DETAILED DESCRIPTION OF THE DRAWINGS

In the following description, the terms "proximal" and "distal" are used in their customary meaning with respect to a human operator.

Figure 1:
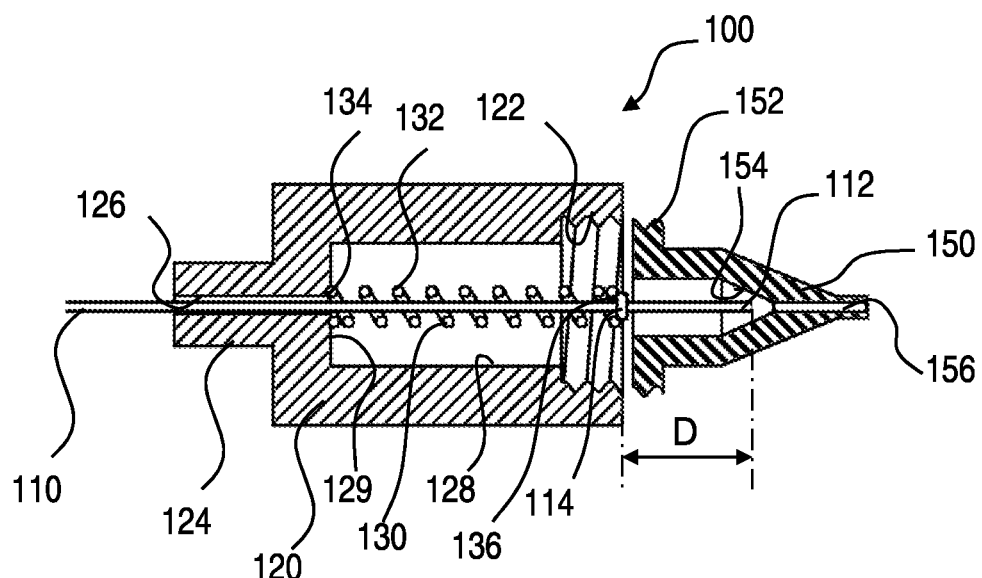
FIG. 1 shows a first embodiment of the delivery device before attachment to a catheter hub.
Figure 2:
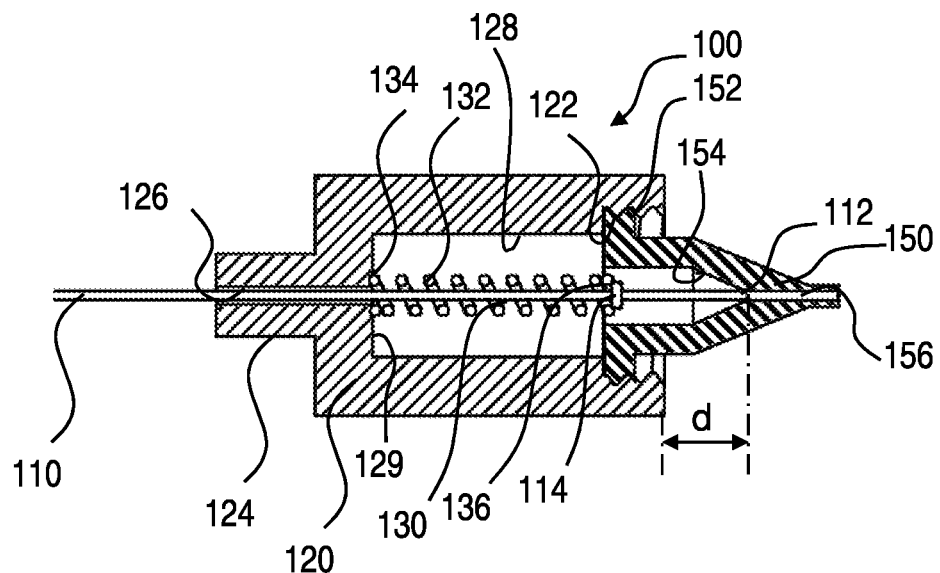
FIG. 2 shows the delivery device of FIG. 1 after attachment to the catheter hub.

FIGS. 1 and 2 show a first embodiment of a delivery device 100 according to the present invention. The delivery device 100 includes a cannula 110, a stability collet 120, and an elastic member 130 formed in this example by a compression spring 132.

The stability collet 120 has a distal attachment portion 122 configured to attach the stability collet to a catheter port 150. In the examples shown in the drawings, the attachment portion 122 is formed by an internal thread on the distal side of the stability collet 120. The attachment portion 122 is dimensioned to engage a corresponding complementary attachment portion 152 on the catheter port 150, shown as an outer thread on a proximal portion of the catheter port 150. The attachment portion 122 may, however, be configured for any other type of connections, such as bayonet connections, snap-in connections, clamping connections, etc., without leaving the scope of the present invention.

The stability collet 120 has a proximal portion 124 surrounding a central longitudinal channel 126. The cannula 110 extends through the longitudinal channel 126 with a distal end 112 of the cannula extending distally beyond the attachment portion 122 and beyond the stability collet 120. The longitudinal channel 126 is dimensioned to allow a longitudinal movement of the cannula 110 in the longitudinal channel 126 while defining a longitudinal path for the cannula 110.

The compression spring 132 extends longitudinally inside the stability collet 120 through a cavity 128 that is distally adjacent the longitudinal channel 126 and extends through the attachment portion 122 to the distal end of the stability collet 120. The compression spring 132 extends coaxially with the cannula 110 and is wound around the cannula 110. The compression spring 132 has a proximal end 134 that is supported at a step 129 formed by a reduction of diameter at the transition from the cavity 128 to the longitudinal channel 126. The compression spring 132 further has a distal end 136 that abuts a stop 114 formed on the cannula 110 distally from the step 129 and from the distal end 136 of the compression spring 132. In the shown embodiments, the stop 114 is shown as a bead fixed on the cannula 110.

It is well within the scope of the present invention to form an alternative stop 114 by affixing the distal end to the cannula 110, for example by an adhesive, or by providing a differently shaped abutment surface.

The stop 114 is placed in such longitudinal position that the compression spring 132, in a relaxed state without external forces, positions the distal end 112 of the cannula 110 distally from the stability collet 120 by a distance D that is greater than a distance d in an assembled state. The distance D, defined by the length of the relaxed compression spring 132, is shown in FIG. 1. Additionally, the length of the compression spring 132 and the location of the stop 114 are configured to allow for a compression of the compression spring 132 by a least the difference between the distance D and the distance d.

In FIG. 2, the catheter port 150 has been properly attached to the stability collet 120. The catheter port 150 has a funnel-shaped catheter well 154 with a longitudinal bore 156. The outer dimensions of the cannula 110 are chosen to be greater than the diameter of the longitudinal bore 156. Thus, when the stability collet 120 is attached to the catheter port 150, the distal end 112 of the cannula 110 is centered by the funnel-shaped catheter well 154 and subsequently abuts the proximal end of the longitudinal bore 156. As the stability collet 120 further approaches the catheter port 150, the compression spring 132 is compressed and biases the cannula 110 toward the longitudinal bore 156 until the stability collet 120 and the catheter port 150 are secured to each other as shown in FIG. 2.

Thus, the compression spring 132 facilitates a proper attachment of the stability collet 120 to the catheter port 150 with a gapless transition from the lumen of the cannula 110 to the longitudinal bore 156 of the catheter port 150. An occluding device, such as a coil (not shown), fed through the cannula 110 is thus smoothly guided into the longitudinal bore 156.

The compression spring 132 has been depicted as one example of a compressible elastic member 130 arranged in the cavity 128. By following the above-described dimensioning rationale, any other compressible elastic member 130 may be arranged in the cavity 128 in analogy to the compression spring 132. Because the stability collet 120 usually does not need to provide a long-term functionality over hundreds of uses, the elastic member 130 may be formed from plastic, foam, or any other elastically compressible structure suitable for a small number of attachments and detachments.

Figure 3:
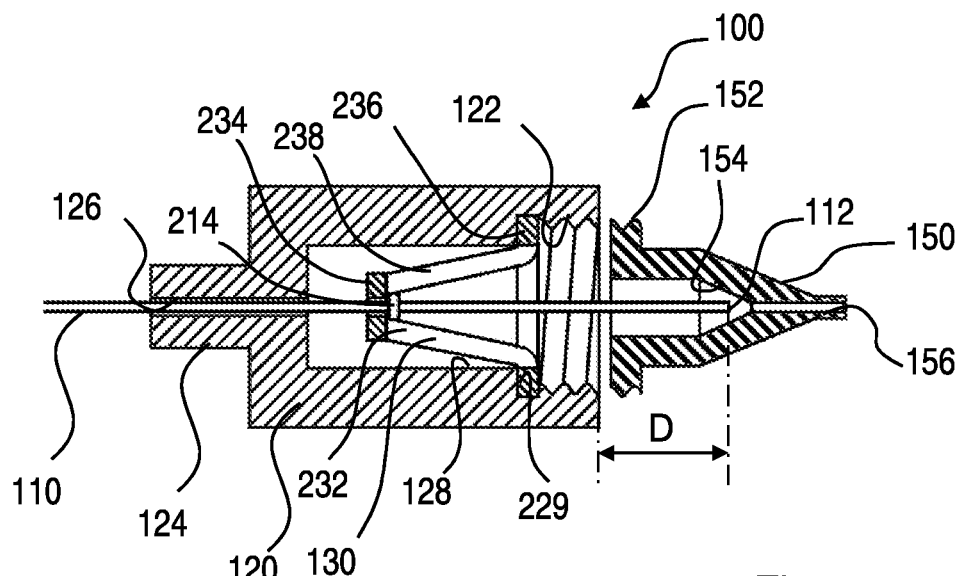
FIG. 3 shows a second embodiment of the delivery device before attachment to the catheter hub.
Figure 4:
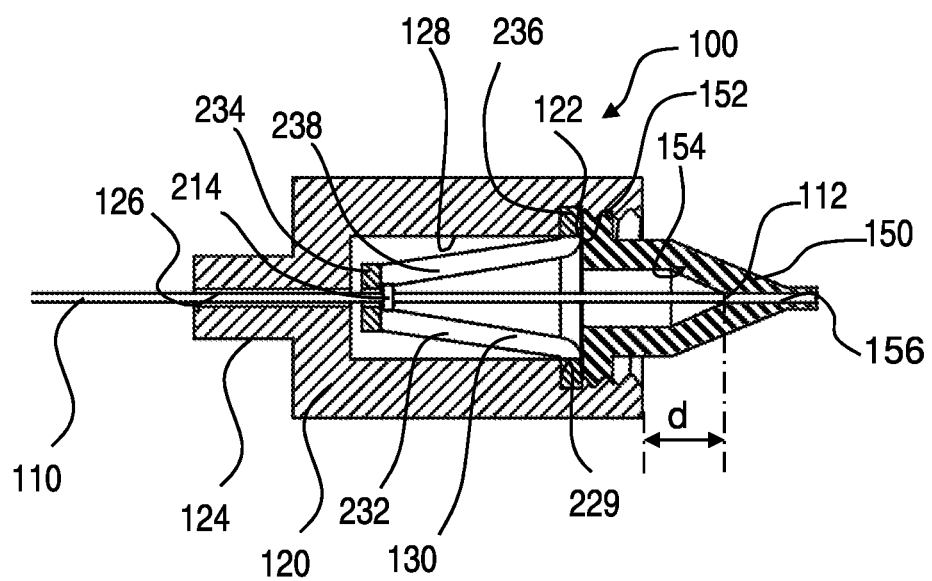
FIG. 4 shows the delivery device of FIG. 3 after attachment to the catheter hub.

FIGS. 3 and 4 show a second embodiment of a delivery device 100 according to the present invention. The delivery device 100 includes the cannula 110, the stability collet 120, and an elastic member 130 formed in this example by an elastomeric expansion element 232.

As previously described in connection with FIGS. 1 and 2, the stability collet 120 has the distal attachment portion 122 configured to attach the stability collet 120 to the attachment portion 152 of the catheter port 150.

The proximal portion 124 of the stability collet 120 surrounds the central longitudinal channel 126. The cannula 110 extends through the longitudinal channel 126 with the distal end 112 of the cannula extending distally beyond the attachment portion 122 and beyond the stability collet 120. The longitudinal channel 126 is dimensioned to allow a longitudinal movement of the cannula 110 in the longitudinal channel 126 while defining a longitudinal path for the cannula 110.

The elastomeric expansion element 232 extends inside the cavity 128 that is distally adjacent the longitudinal channel 126 and extends through the attachment portion 122 to the distal end of the stability collet 120. The elastomeric expansion element 232 extends coaxially with the cannula 110. The elastomeric expansion element 232 has a proximal end 234 that is supported at a stop 214 formed on the cannula 110 distally from the proximal end 234. The elastomeric expansion element 232 further has a distal end 236 retained by a step 229 of the stability collet 120 at the transition between the attachment portion 122 and the cavity 128. In the shown embodiment, the stop 214 is shown as a bead fixed on the cannula 110.

It is well within the scope of the present invention to form an alternative stop 214 by affixing the proximal end 234 of the elastomeric expansion element 232 to the cannula, for example by adhesion, or by providing a differently shaped abutment surface. In the embodiment shown, the elastomeric expansion element 232 has a plurality of stretchable bands 238 extending from the distal end 236 to the proximal end 234

The embodiment of FIGS. 3 and 4 further shows a dual function of the elastomeric expansion element 232. The distal end 236 is ring-shaped and embedded at the proximal end of the attachment portion 122. Thus, the distal end 236 additionally serves as a sealing element between the attachment portion 122 of the stability collet 120 and the attachment portion 152 of the catheter port 150. This sealing function is optional. Any other distal retention of the distal end 236 of the elastomeric expansion element 232 can establish the elastic function of the elastomeric expansion element 232 without leaving the scope of the present invention.

The stop 214 is placed in such longitudinal position that the elastomeric expansion element 232, in a relaxed state without external forces, positions the distal end 112 of the cannula 110 distally from the stability collet 120 by the distance D that is greater than a distance d in an assembled state. The distance D, defined by the length of the relaxed length of the stretchable bands 238 of the elastomeric expansion element 232, is shown in FIG. 3. Additionally, the length of the elastomeric expansion element 232 and the location of the stop 214 are configured to allow for an expansion of the elastomeric expansion element 232 by a least the difference between the distance D and the distance d.

In FIG. 4, the catheter port 150 has been properly attached to the stability collet 120. As in FIGS. 1 and 2, the catheter port 150 includes the funnel-shaped catheter well 154 with the longitudinal bore 156. The outer dimensions of the cannula 110 are again chosen to be greater than the diameter of the longitudinal bore 156. Thus, when the stability collet 120 is attached to the catheter port 150, the distal end 112 of the cannula 110 is centered by the funnel-shaped catheter well 154 and subsequently abuts the proximal end of the longitudinal bore 156. As the stability collet 120 further approaches the catheter port 150, the elastomeric expansion element 232 is expanded due to the distal movement of the stop 214 and biases the cannula 110 toward the longitudinal bore 156 until the stability collet 120 and the catheter port 150 are secured to each other as shown in FIG. 4. The distal end 236 additionally seals the transition between the attachment portion 122 of the stability collet 120 and the attachment portion 152 of the catheter port 150.

Thus, the elastomeric expansion element 232 facilitates a proper attachment of the stability collet 120 to the catheter port 150 with a gapless transition from the lumen of the cannula 110 to the longitudinal bore 156 of the catheter port 150. An occluding device, such as a coil (not shown) fed through the cannula 110 is thus smoothly guided into the longitudinal bore 156.

The elastomeric expansion element 232 has been depicted as one example of an expandable elastic member 130 arranged in the cavity 128. By following the above-described dimensioning rationale, any other expandable elastic member 130 may be arranged in the cavity 128 in analogy to the elastomeric expansion element 232. The expandable elastic member 130 may also be formed from plastic, foam, or any other elastically expandable structure suitable for a small number of attachment and detachment operations.

Figure 5:
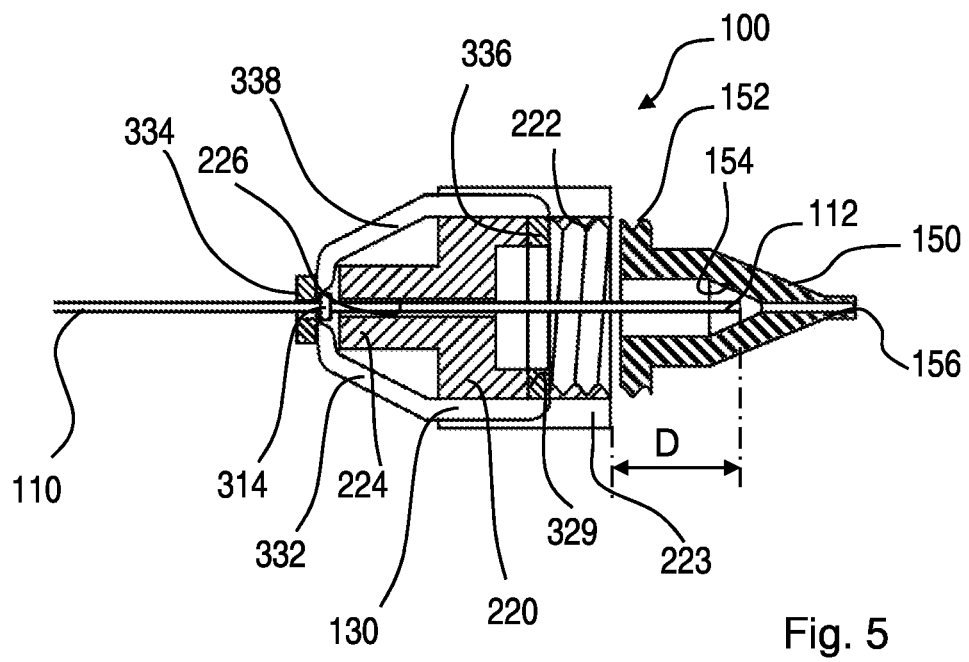
FIG. 5 shows a third embodiment of the delivery device before attachment to the catheter hub.
Figure 6:
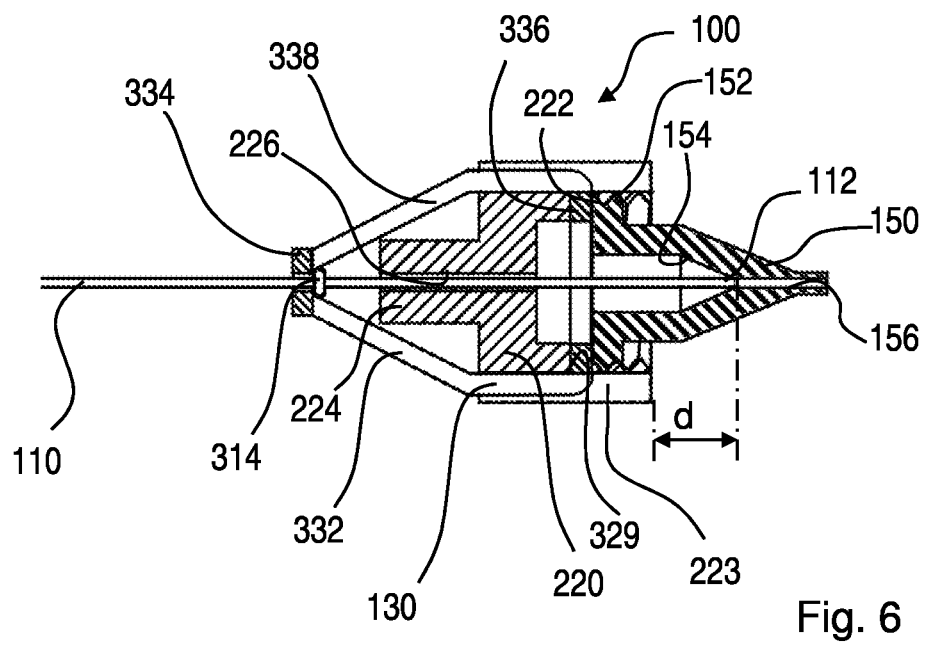
FIG. 6 shows the delivery device t of FIG. 5 after attachment to the catheter hub.

FIGS. 5 and 6 show a third embodiment of a delivery device 100 according to the present invention. The embodiment of FIGS. 5 and 6 incorporates an elastomeric expansion element 332 that is partially arranged outside a stability collet 220. Because the elastomeric expansion element 332 does not need to expand inside the stability collet 220, the stability collet 220 may have a shorter longitudinal dimension than the stability collet 120 of FIGS. 1 through 4. The length of the stability collet 220 of the shown embodiment is mostly defined by the longitudinal channel 226 in the proximal portion 224 of the stability collet and of the attachment portion 222.

The elastomeric expansion element 332 has a distal end 336 retained inside the stability collet 220 at a step 329 of the stability collet 220 at the proximal end of the attachment portion 222. The elastomeric expansion element 332 further has a proximal end 334 that is supported at a stop 314 formed on the cannula 110 proximally from the stability collet 220. In the shown embodiment, the stop 314 is shown as a bead fixed on the cannula 110.

It is well within the scope of the present invention to form an alternative stop 314 by affixing the proximal end 334 of the elastomeric expansion element 332 to the cannula, for example by adhesion, or by providing a differently shaped abutment surface.

The embodiment of FIGS. 5 and 6 further shows a dual function of the elastomeric expansion element 332. The distal end 336 is ring-shaped and embedded at the proximal end of the attachment portion 222. Thus, the distal end 336 additionally serves as a sealing element between the attachment portion 222 of the stability collet 120 and the attachment portion 152 of the catheter port 150. This sealing function is optional. Any other distal retention of the distal end 236 of the elastomeric expansion element 232, for example on the outside of the stability collet 220, can establish the elastic function of the elastomeric expansion element 232 without leaving the scope of the present invention.

In the embodiment shown, the elastomeric expansion element has a plurality of stretchable bands 338 extending from the distal end 336 outward through channels 223 in the stability collet 220 to the proximal end 234. The stop 314 is placed in such longitudinal position that the elastomeric expansion element 232, in a relaxed state without external forces, positions the distal end 112 of the cannula 110 distally from the stability collet 220 by the distance D that is greater than the distance d in the assembled state.

In this embodiment, it should be noted that the relaxed state does not require that the elastomeric expansion element is free of tension. The elastomeric expansion element may be stretched even in the relaxed state. Because the stop 314 defines the shortest length that can be obtained by the stretchable bands 338, the stretchable bands 338 themselves do not define the relaxed state. Thus, the relaxed state of the stretchable bands 338 is defined by the position of the stop 334. The stretchable bands 338 only need to be further expandable to move the cannula 110 from the position shown in FIG. 5 to the position shown in FIG. 6. The distance D, defined by the relaxed state of the elastomeric expansion element 232, is shown in FIG. 5, while the distance d defined by the assembled position is shown in FIG. 6.

In FIG. 6, the catheter port 150 has been properly attached to the stability collet 220. As in FIGS. 1 and 2, the catheter port 150 includes the funnel-shaped catheter well 154 with the longitudinal bore 156. The outer dimensions of the cannula 110 are again chosen to be greater than the diameter of the longitudinal bore 156. Thus, when the stability collet 220 is attached to the catheter port 150, the distal end 112 of the cannula 110 is centered by the funnel-shaped catheter well 154 and subsequently abuts the proximal end of the longitudinal bore 156. As the stability collet 220 further approaches the catheter port 150, the elastomeric expansion element 332 is expanded due to the distal movement of the stop 314 and biases the cannula 110 toward the longitudinal bore 156 until the stability collet 220 and the catheter port 150 are secured to each other as shown in FIG. 6. In FIG. 6, the distal end 336 of the elastomeric expansion element 332 seals the transition between the attachment portion 222 of the stability collet 220 and the attachment portion 152 of the catheter port 150.

Figure 7:
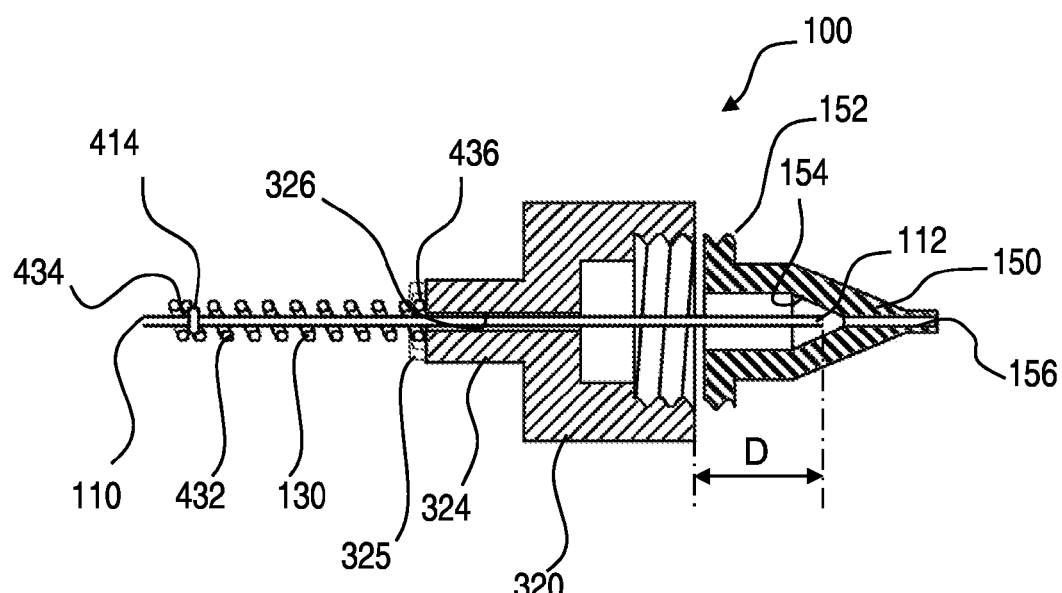
FIG. 7 shows a fourth embodiment of the delivery device before attachment to the catheter hub.
Figure 8:
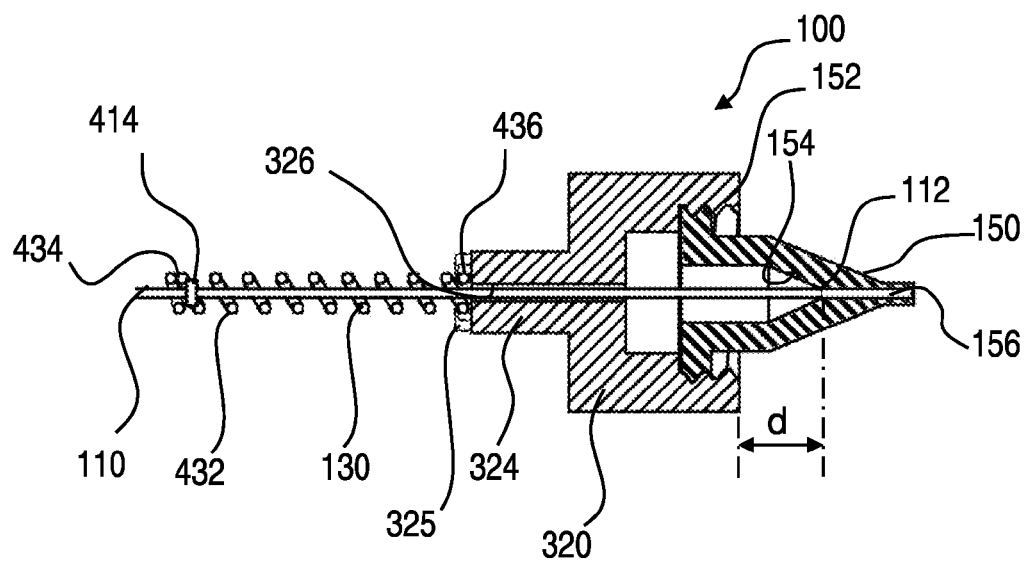
FIG. 8 shows the delivery device of FIG. 7 after attachment to the catheter hub.

FIGS. 7 and 8 show a fourth embodiment of a delivery device 100 according to the present invention. The embodiment of FIGS. 7 and 8 incorporates an expansion spring 432 arranged outside a stability collet 320. Because the expansion spring 432 does not need to expand inside the stability collet 320, the stability collet 320 may have a shorter longitudinal dimension than the stability collet 120 of FIGS. 1 through 4. The length of the stability collet 320 of the shown embodiment is mostly defined by the longitudinal channel 326 in the proximal portion 324 of the stability collet and of the attachment portion 322.

The expansion spring 432 has a distal end 436 retained by a retainer 325 formed on the proximal side of the stability collet 320. Any other distal retention of the distal end 436 of the expansion spring 432, for example on the outside of the stability collet 320, can establish the elastic function of the expansion spring 432 without leaving the scope of the present invention. The expansion spring 432 further has a proximal end 334 that is supported at a stop 414 formed on the cannula 110 proximally from the stability collet 220. In the shown embodiment, the stop 414 is shown as a bead fixed on the cannula 110 distally from the proximal end 434 of the expansion spring 432.

It is well within the scope of the present invention to form an alternative stop 414 by affixing the proximal end 434 of the expansion spring 432 to the cannula, for example by adhesion, or by providing a differently shaped retainer on the cannula 110. Any other distal retention of the distal end 436 of the expansion spring 432, for example on the outside of the stability collet 320, can establish the elastic function of the expansion spring 432 without leaving the scope of the present invention.

The stop 414 is placed in such longitudinal position that the expansion spring 432, in a relaxed state without external forces, positions the distal end 112 of the cannula 110 distally from the stability collet 320 by the distance D that is greater than the distance d in the assembled state. The distance D, defined by the relaxed state of the expansion spring 432, is shown in FIG. 7, while the distance d defined by the assembled position is shown in FIG. 8.

In FIG. 6, the catheter port 150 has been properly attached to the stability collet 320. As in FIGS. 1 and 2, the catheter port 150 includes the funnel-shaped catheter well 154 with the longitudinal bore 156. The outer dimensions of the cannula 110 are again chosen to be greater than the diameter of the longitudinal bore 156. Thus, when the stability collet 320 is attached to the catheter port 150, the distal end 112 of the cannula 110 is centered by the funnel-shaped catheter well 154 and subsequently abuts the proximal end of the longitudinal bore 156. As the stability collet 320 further approaches the catheter port 150, the expansion spring 432 is expanded due to the distal movement of the stop 414 and biases the cannula 110 toward the longitudinal bore 156 until the stability collet 320 and the catheter port 150 are secured to each other as shown in FIG. 8.

Figure 9:
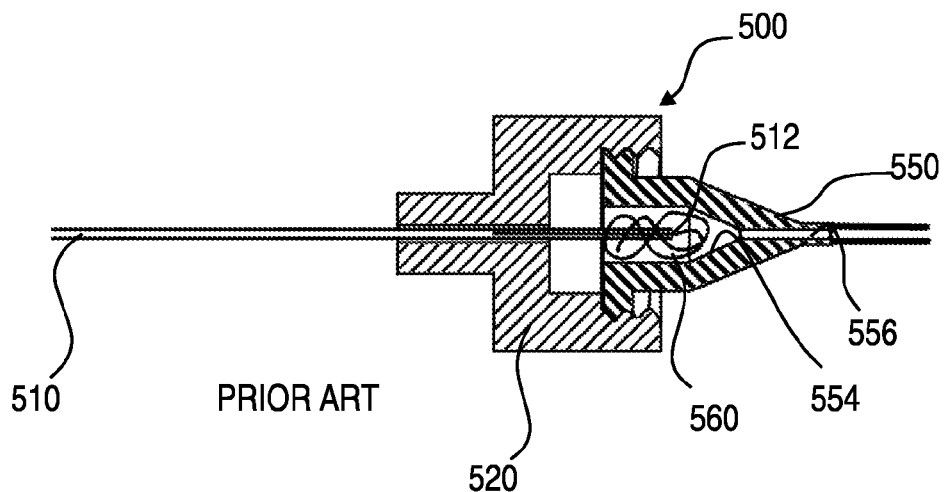
FIG. 9 shows a prior-art delivery device with an elongated occlusion device after improper attachment to the catheter hub.

Now referring to FIG. 9, a delivery device 500 is shown that schematically represents a prior art delivery device. A cannula 510 is longitudinally movable relative to a stability collet 520. The stability collet 520 is attached to a catheter port 550 that has a distal longitudinal bore 556. The cannula 510 has a distal end 512 distally extending past the stability collet 520. Because the cannula 510 is longitudinally movable within the stability collet, it is conceivable that the cannula may be placed so that the distal end 512 out of contact with the longitudinal bore 556 after attaching the catheter port. In such a situation, an elongated occlusion device to be delivered into the longitudinal bore 556 with a wire guide (not shown) may instead curl into a catheter well 554 without entering the longitudinal bore 556.

Figure 10:
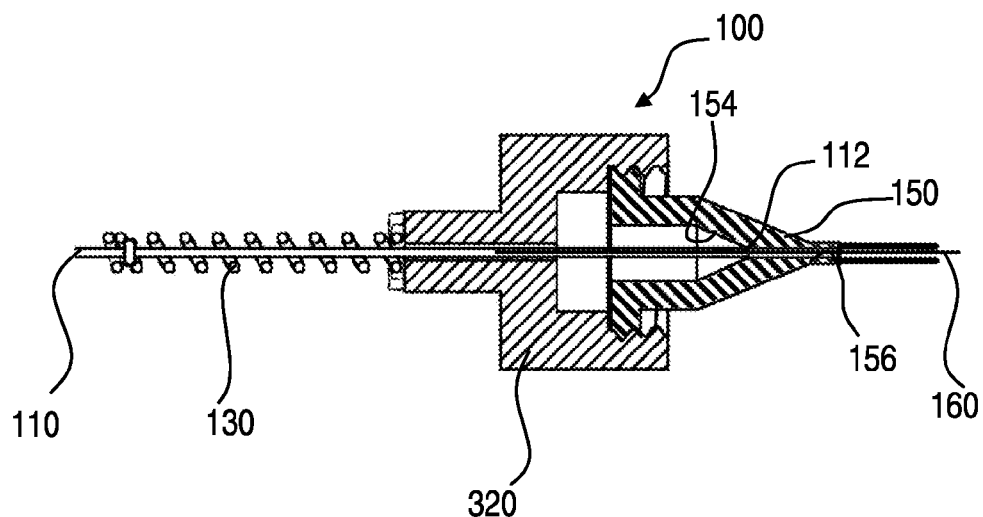
FIG. 10 shows the delivery device of FIGS. 8 and 9 with an elongated occlusion device after proper attachment to the catheter hub.

In contrast, FIG. 10 shows, by the example of the embodiment of FIGS. 7 and 8, how the delivery device 100 automatically brings the distal end 112 of the cannula 110 into contact with the longitudinal bore 156 of the catheter port 150 by incorporating the elastic member 130 biasing the cannula 110 distally relative to the stability collet 320. The funnel shape of the well 154 aides with radially aligning the cannula 110 with the longitudinal bore 156 so that an elongated occluding device 160 can be pushed directly from the cannula 110 into the longitudinal bore 156. Optionally, the stability collet may be removed before the coil is further advanced to an intended site in a patient body.

The foregoing description of various embodiments of the invention has been presented for purposes of illustration and description. It is not intended to be exhaustive or to limit the invention to the precise embodiments disclosed. Numerous modifications or variations are possible in light of the above teachings, and the properties of one embodiment may be modified with properties of another. The embodiments discussed were chosen and described to provide the best illustration of the principles of the invention and its practical application to enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A delivery device for delivering material into a catheter through a catheter port, the delivery device comprising: a cannula having a generally tubular shape and a distal end; a stability collet having a distal attachment portion configured to attach the stability collet to a catheter port and a longitudinal channel through which the cannula extends, the longitudinal channel being dimensioned to allow a longitudinal movement of the cannula in the longitudinal channel; and an elastic member acting between the cannula and the stability collet, the elastic member biasing the cannula distally relative to the stability collet, the elastic member having a relaxed state absent from external forces while inside the stability collet and a tensioned state, the relaxed state positioning the distal end of the cannula distally from the tensioned state.

2. The delivery device of claim 1, wherein the elastic member is a resilient spring.

3. The delivery device of claim 2, wherein the resilient spring is a helical spring.

4. The delivery device of claim 2, wherein the resilient spring is a compression spring with a proximal spring end restricted by the longitudinal channel of the stability collet and with a distal spring end restricted by a stop on the cannula.

5. The delivery device of claim 1, wherein the entire elastic member is inside the stability collet.

6. The delivery device of claim 1, wherein the elastic member is in the tensioned state when the distal end of the cannula is in a position relative to the stability collet that corresponds to a position that the distal end of the cannula occupies when a catheter port is attached to the stability collet.

7. The delivery device of claim 1, wherein the elastic member acts on the cannula via a stop fixedly connected to the cannula, the stop restricting a longitudinal movement of one end of the elastic member relative to the cannula in a least one direction.

8. The delivery device of claim 1, wherein the elastic member is fixedly attached to at least one of the cannula and the stability collet.

9. The delivery device of claim 1, further comprising an elongated occluding device stored in the cannula.

\* \* \* \* \*